(12) United States Patent
Mostafa

(10) Patent No.: US 10,034,744 B1
(45) Date of Patent: Jul. 31, 2018

(54) DEVICE FOR TREATMENT OF CORNEAL DEFECTS

(71) Applicant: Islam Mahmoud Hamdi Ibrahim Mostafa, Jeddah (SA)

(72) Inventor: Islam Mahmoud Hamdi Ibrahim Mostafa, Jeddah (SA)

( * ) Notice: Subject to any disclaimer, the term of this patent is extended or adjusted under 35 U.S.C. 154(b) by 10 days.

(21) Appl. No.: 15/459,902

(22) Filed: Mar. 15, 2017

(51) Int. Cl.
*A61F 2/14* (2006.01)

(52) U.S. Cl.
CPC ............ *A61F 2/142* (2013.01); *A61F 2/145* (2013.01); *A61F 2/147* (2013.01); *A61F 2230/0013* (2013.01); *A61F 2250/0026* (2013.01); *A61F 2250/0091* (2013.01)

(58) Field of Classification Search
CPC .......... A61F 2/142; A61F 2/145; A61F 2/147
USPC ......................................... 623/5.12
See application file for complete search history.

(56) References Cited

U.S. PATENT DOCUMENTS

| | | | | |
|---|---|---|---|---|
| 5,824,086 A * | 10/1998 | Silvestrini | ............... | A61F 2/147 623/5.11 |
| 6,006,756 A * | 12/1999 | Shadduck | ............... | A61F 2/147 128/899 |
| 6,138,307 A * | 10/2000 | McDonald | ............... | A61F 2/147 623/4.1 |
| 6,206,919 B1 * | 3/2001 | Lee | ............... | A61F 2/147 623/4.1 |
| 2002/0058996 A1 * | 5/2002 | Silvestrini | ............... | A61F 2/147 623/5.12 |
| 2004/0073303 A1 * | 4/2004 | Schanzlin | ............... | A61F 2/147 623/5.16 |
| 2009/0076601 A1 * | 3/2009 | Daxer | ............... | A61F 2/147 623/5.16 |
| 2009/0306773 A1 * | 12/2009 | Silversrini | ............... | A61F 2/147 623/5.11 |
| 2014/0074232 A1 * | 3/2014 | Soares | ............... | A61F 2/147 623/5.12 |
| 2016/0038276 A1 * | 2/2016 | Albertazzi | ............... | A61F 9/007 623/5.12 |

* cited by examiner

*Primary Examiner* — David H Willse
*Assistant Examiner* — Javier Blanco
(74) *Attorney, Agent, or Firm* — Hayes Soloway PC

(57) ABSTRACT

There is provided an implant which is utilized in the treatment of corneal defects and conditions, such as for example Keratoconus. An intracorneal implant is provided having a first and second curved segment, which form a ring-like device. The first and second curved segments of the ring-like device are detached. The ring-like device has an inner diameter in the range of 4.95 mm to 5.25 mm and an outer diameter in the range of 6.8 mm to 7.1 mm. The first and second curved segments are symmetrical in cross section and are comprised of a transparent material.

5 Claims, 2 Drawing Sheets

DEVICE FOR TREATMENT OF CORNEAL DEFECTS

CROSS REFERENCE TO RELATED APPLICATIONS

Not Applicable

BACKGROUND

Field of Invention

The present invention relates to a device used for the treatment of a condition of the cornea, and more particularly to a device for the treatment of Keratoconus.

Description of Related Art

The cornea of the eye is the clear outer layer and the first lens of the eye. Normally the cornea has a dome like shape. In certain instances, the structure of the cornea is not strong enough to hold this shape and the cornea bulges out in a cone-like shape. This condition is called Keratoconus.

Tiny fibers of protein in the eye called collagen help hold the cornea in place and keep it from bulging. When these fibers become weak, they cannot hold the shape and the cornea becomes progressively more cone shaped.

Keratoconus is known to be progressive corneal condition wherein alterations of the morphology of the tissue, have a negative impacts the patient's visual function and optical quality. The changes in the shape of the cornea can happen quickly or may occur over several years. The changes can result in blurred vision, glare and halos at night, and the streaking of lights.

With severe Keratoconus, the stretched collagen fibers can lead to severe scarring. If the back of the cornea tears, it can swell and take many months for the swelling to go away. This often causes a large corneal scar.

Keratoconus can negatively impact vision in two ways:
As the cornea changes from a dome shape to a cone shape, the smooth surface becomes wavy. This is called irregular astigmatism.
As the front of the cornea expands, vision becomes more nearsighted. That is only up close objects can be seen clearly. Anything too far away will look like a blur.

As the condition is progressive, without medical intervention the morphology of the cornea worsens, further negatively impacting a patient's vision.

Currently, there are several medical procedures for the management of this condition, such as contact lens wearing, corneal collagen cross-linking (CXL), and intracorneal ring segments (ICRS) implantation.

ICRS are small devices made of synthetic material, which are surgically implanted within the corneal stroma (between the layers of the cornea) in order to induce a change in the geometry and the refractive power of the corneal tissue. ICRS are typically arc shaped and can include a single 360 degree circular implant or smaller (210 degree) or can be separated into two arc segments of varying arc length (commonly expressed in degrees).

The common characterization of currently available ICRS includes several important variables, which have a direct impact on the corrective power of the ICRS, and a patient's quality of vision while the ICRS remain implanted within the corneal stroma. These variables include the arc segment degrees, the inner diameter between the arc segments, the outer diameter, and the cross sectional shape of the segments.

There are several commercially available ICRS currently utilized for implantation and correction of Keratoconus. Each of these ICRS have different arc length, inner diameter, outer diameter, cross-sectional shape, and segment thickness.

The choice of ICRS for implantation often depends on the surgeon's specifications for what level of correction is required, based on the severity of the condition. The arc segments, once implanted aid in stopping the progression of the condition by pulling on the base of the cone, to bring the apex down and reshape the cornea more closely to a normal dome shape.

Currently available ICRS have several drawbacks, which have kept them from being completely successful in correction of the Keratoconus. Typically an ICRS with a small inner diameter (e.g. 4.6 mm) can have more effective influence in correcting the cone shape of the cornea, but it causes severe visibility issues for patients. For example the patient will be more aware of the ICRS as it can come within their field of vision, and thus be visibly perceived by the patient. This effect can be exacerbated at night time as pupils will be more dilated in darker conditions, thereby significantly effecting vision of a patient at night time.

With larger inner diameter ICRS, there is less chance of the ICRS being perceived by the patient and interfering in night time vision, but the effectiveness of the ICRS in correcting the cone like shape of the cornea is also reduced. The larger the inner diameter of the ICRS, the less effective the corrective nature of the implant becomes.

Another drawback of ICRS with larger inner diameters is that often times, they require supplemental solutions, such as for example the patient may further need corneal collagen cross-linking (CXL).

Based on the current drawbacks of existing ICRS designs, there remains a need in the field for an ICRS device which is not perceived by the patient, and does not cause the patient blurry vision at nighttime. There further remains a need for an ICRS device which is effective in correcting Keratoconus and does not require does not require supplemental therapy. Additionally, there remains a need for an ICRS which finds a balance between effectively treating Keratoconus while not causing the patient any optical discomfort or optical hindrance.

It is an objective of the present invention to provide an ICRS which is easy to implant by a surgeon.

It is a further objective of the present invention to provide an ICRS which effectively solves the current drawbacks of current ICRS designs discussed above.

SUMMARY OF INVENTION

The present invention is directed towards a device used for the treatment of corneal disorders or defects, and particularly for the treatment of Keratoconus. In one embodiment of the present invention there is provided an intracorneal implant, having a first curved segment, and a second curved segment, the first and second curved segments forming a ring-like device.

In one embodiment, the first and second curved segments are detached and have an arc length of in the range of about 150 to 165 degrees. The ring-like device, which is comprised of the first and second curved segments has an inner diameter ranging between 4.95 mm to 5.30 mm, and an outer diameter ranging between 6.8 mm to 7.1 mm. The first and second curved segments have a height ranging between 150 micrometers to 300 micrometers.

The first and second curved segments have a symmetrical cross section and have rounded end portions.

In one embodiment, the ring-like device has an inner diameter ranging between 5.0 mm to 5.25 mm, and preferably 5.20 mm.

In a further embodiment, there is provided an intracorneal implant wherein the ring-like device has an outer diameter ranging between 6.9 mm to 7.1 mm, and preferably 7.0

In another embodiment, an intracorneal implant is provided wherein the first and second ring segments have a height ranging between 150 micrometers to 300 micrometers, and preferably in the range of 200 to 250 micrometers. The height of the first curved segment can be the same as that of the curved segment, or the two curved segments can have different heights.

In one embodiment, an intracorneal implant is provided wherein the first and second curved segments have an arc length of 160 degrees, although other embodiments will also be described herein, wherein the are length is greater, specifically 210 degrees. In this embodiment the intracorneal implant includes only one curved segment, and not two as in the previously described embodiments.

In one embodiment, the intracorneal implant has a symmetrical cross section of the first and second curved segments. The symmetrical cross section is provided by a top and bottom wall of the curved segments, both of which are flat in shape. The inner and outer side walls of the curved segments however are of rounded shape.

The first and second curved segments are preferably comprised of a transparent material. In one embodiment the transparent material is a polymer. In a preferred embodiment the transparent polymer is Poly methyl methacrylate (PMMA).

In a further embodiment, the first and second curved portions further comprise apertures, located in proximity of the rounded end portions. The apertures are in the shape of circular holes, which aid in the position of the first and second curved portions during implantation by a surgeon within the intracorneal space.

Further embodiments relating to the intracorneal implant will be described in more detail in the "Detailed Description" section below. The various and advantages of the present invention will become apparent from the following detailed description and accompanying drawings, showing the principles of the invention.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

In the drawings.

DETAILED DESCRIPTION

Figure 1:
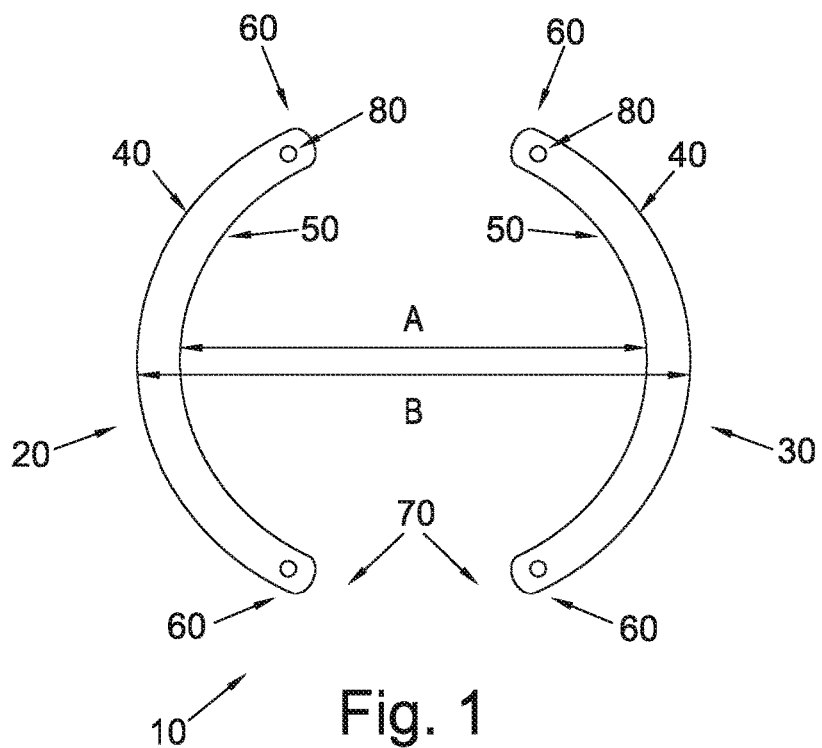
FIG. 1 illustrates a top view of one embodiment of the present invention.

In the following Detailed Description, reference is made to the accompanying drawings, which form a part hereof, and in which is shown by way of illustration specific embodiments in which the invention may be practiced. Wherever possible, the same reference numbers are used in the drawings and the description to refer to the same or like parts. Directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The present invention as illustrated in FIG. 1, pertains to an intracorneal implant which is utilized for correction of corneal defects, and more particularly for Keratoconus. As shown in FIG. 1, the intracorneal implant has a first curved segment 20 and a second curved segment 30. Both of these curved segments form a ring-like device 10 as depicted in FIG. 1, which is implanted in a patient's intracorneal space.

The first curved segment 20 and the second curved segment 30, making up the ring-like device 10 have an arc length in the range of about 150 to 165 degrees, and preferably about 160 degrees. The are length refers to the curvature distance of the segments 20 and 30. The smaller the arc length, the shorter the length of the curved segments 20 and 30, thereby covering a smaller area of the cornea. Whereas a longer arc length, for example 210 degrees covers a greater area of the cornea. A further embodiment relating to a curved segment with a longer are length, will be described in later sections. In this embodiment, the are length of the curved segments 20 and 30 is 160 degrees.

As can be seen, the first and second curved segments 20 and 30 are detached from each other. The ring-like device 10, formed from the curved segments 20 and 30 has an inner diameter, represented by arrow A in FIG. 1, which is shown as the distance between the inner side walls 50 of the first curved segment 20 and the second curved segment 30. In one embodiment, this inner diameter, A, can range between 4.95 mm to 5.30 mm, from 5.0 mm to 5.25 mm, from 5.1 to 5.20 mm, and preferably the inner diameter A is 5.2 mm.

Also seen in FIG. 1, is an outer diameter, depicted by arrow B, which is shown as the distance between the outer side walls 40 of the first curved segment 20 and the second curved segment 30, making up the ring-like device 10. The outer diameter B, ranges from between 6.8 mm to 7.1 mm. In another embodiment, the outer diameter B ranges from 6.9 mm to 7.0 mm, and in a preferred embodiment, the outer diameter B is 7.0 mm.

Also shown in FIG. 1 are the end portions 60 of the curved segments 20 and 30. Both of the curved segments 20 and 30 have two end portions 60 each. The end portions 60 have a rounded end walls 70, as can be seen in FIG. 1. Located near the end portions 60 are apertures 80, with each end portion 60 having one aperture 80 located in its proximity. These apertures 80 are utilized for positioning purposes during implantation, i.e. during the surgical procedure. A surgeon is able to utilize these apertures in order to maneuver and move the curved segments 20 and 30 in the correct position in the intracorneal space of the patient. The apertures 80 are defined by a hollow circular space, which extend from the top wall 90 to the bottom wall 100 of the curved segments 20 and 30 (top wall 90 and bottom wall 100 are depicted in FIG. 2).

Figure 2:
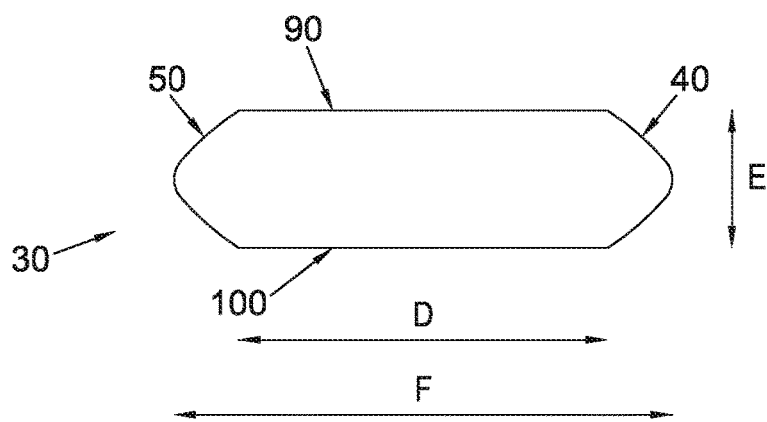
FIG. 2 illustrates a cross-sectional view of one embodiment of the present invention.

Moving now to FIG. 2, a cross-sectional view of the curved segments 20 and 30 is shown. Only one curved segment is depicted for brevity and simplicity, however both curved segments 20 and 30 have an identical shape, although the dimensions of either curved segment 20 or 30 can differ from each other. A determination on the dimensions of each segment is conducted by the surgeon to determine the appropriate corrective need for a particular patient. Therefore, both curved segments can have identical dimensions, or they may have different dimensions, and particularly with respect to the height of the segments, based on the determinations of the surgeon. For purposes of this discussion, the cross-sectional attributes of curved segment 30 will be described in detail. One of ordinary skill in the art is to understand that, the same discussion also pertains to curved segment 20, as both segments are intended to have an identical design and dimensions.

In FIG. 2, a cross-sectional view of curved segment 30 is shown. The inner side wall 50 is depicted on the left side of FIG. 2, and the outer side wall 40 is shown on the right side, corresponding also to the curved segment 30 shown in FIG. 1.

The curved segment 30 has a top wall 90 and a bottom wall 100, as shown in FIG. 2. As can be seen, the curved segment 30 has a symmetrical shape and cross section, whether taken from top to bottom, or from left to right. The same configuration and shape also applies to curved segment 20 (not shown). The top wall 90 and bottom wall 100 have a flat shape, while the inner wall 50 and outer wall 40 have a curved shape, protruding outwards from the body of the curved segment 30. Due to this symmetry, the curved segments 20 and 30 can be implanted with either side, facing down onto the cornea, either top wall 90 or bottom wall 100. Therefore these sides are interchangeable, and make for the implantation procedure to be easier than currently existing implants which do not have a symmetrical cross section. Therefore, a surgeon during the surgical procedure does not have to first determine which side of the curved segments 20 and 30 has to be placed facing down onto the cornea, as either side can be placed facing down, due to the symmetry of the ring-like device 10. This in turn makes the surgical procedure quicker and less prone to incorrect implantation.

The curved segment 30, depicted in FIG. 2, has a height as shown by arrow E. The height E can range between 150 micrometers to 300 micrometers. In one embodiment the height E of the curved segments 20 and 30 can be 150 micrometers. In another embodiment the height E is 200 micrometers. In a further embodiment the height E is 250 micrometers, and in an additional embodiment the height E is 300 micrometers. In a further embodiment, both the curved segments 20 or 30 can have a different height from each other. For example, the first curved segment 20 may have a height of 200 micrometers, while the second curved segment 30 has a height of 250 micrometers. The determination of the appropriate height of each segment is made by the surgeon and the type of correction required for each specific patient. This is because the height of the curved segments 20 and 30 can have an effect on the degree of correction provided by the implant. The more correction that is necessary, the higher the height E of the curved segments 20 and 30 may be chosen by the surgeon during implantation. The degree of corrective effect which is necessary is determined by the surgeon and the implantation of the appropriately sized right like device is implemented accordingly.

The cross sectional view of curved segment 30 as shown in FIG. 2 also depicts a first width shown by arrow D. This width D corresponds to the width of the top wall 90 and bottom wall 100, which should be identical in dimension. The width D can vary, although preferably it measures at 0.75 millimeters. The width of the entire curved segment 30, as shown by arrow F, is the measured distance between the outermost point of the rounded inner wall 50 to the outermost point of the rounded outer wall 40. This width F can also vary, but is preferably 0.85 millimeters.

In an additional embodiment, the intracorneal implant of the present invention can comprise a single curved segment, instead of utilizing two segments which form a ring-like device. In certain instances, the surgeon may determine, based on the curvature of the corneal cone, that a single segment would be best suited for corrective purposes for a particular patient. This single segment can have all the aforementioned dimensions, shape, cross-sectional symmetry, and can have an arc length greater than 160, such as for example an arc length of 210 degrees. Therefore, the illustration in FIG. 2, also applies to this embodiment, wherein the intracorneal implant is solely a single implanted curved segment. The height E, and the widths D and F, are still in the dimensions and ranges as described in the above embodiments, however the arc length is longer, at 210 degrees instead of 160 degrees. Because in this embodiment the curved segment has a longer arc length, covering a greater part of the intercorneal space, it is implanted singularly on its own, instead of as a two segment set, making up a ring-like device.

The intracorneal implant, whether comprised of a single segment, or comprised of the two curved segments 20 and 30 is preferably composed of a transparent material, such as a transparent polymer material. The transparency of the material is an important feature so as not to inhibit the optical function of the corneal space. In one embodiment, the transparent material can be Poly (methyl methacrylate) (PMMA).

Figure 3:
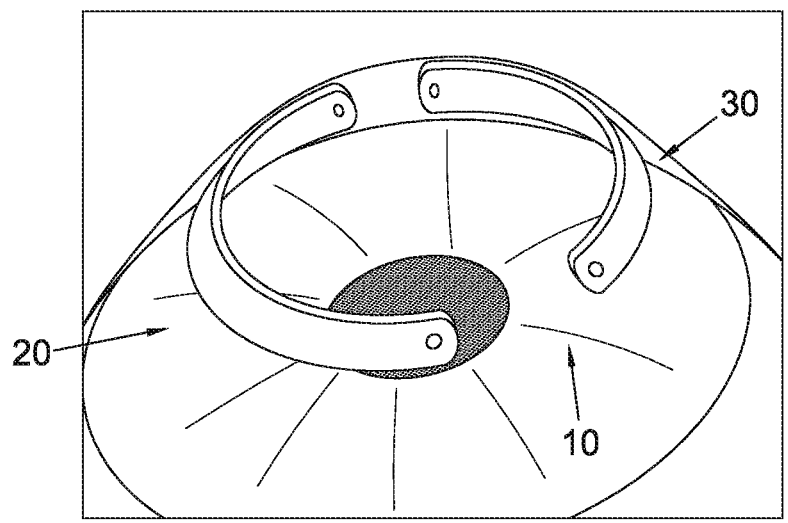
FIG. 3 illustrates a perspective view of one embodiment of the present invention.

Moving now to FIG. 3, the ring-like device 10 making up the intracorneal implant of the present invention, is shown in its implanted location in the intracorneal space of a patient suffering from a corneal defect, and particularly Keratoconus.

As can be seen in FIG. 3 the curved segment 20 and curved segment 30 are positioned in a circular fashion facing each other, and forming the ring-like device 10 of the present invention, within the intracorneal space. The surgical procedure for placement of such an implant is already familiar to one skilled in the art and for purposes of brevity will not be detailed in the present disclosure.

In contrast to existing intracorneal implant devices, the inventor of the present invention has thus shown an intracorneal implant 10 which has specific dimensions, shape and symmetry, so as to provide the maximum benefits to a patient, while removing the current drawbacks of existing devices.

With the specific inner diameter A ranging between 4.95 mm to 5.2 mm, and outer diameter B ranging between 6.8 mm to 8.1 mm, the intracorneal implant provides a smaller optical zone when implanted, as compared to existing devices. This smaller optical zone allows for a higher degree of correction. However, the optical zone is not small enough so to be perceived by the patient, particularly at times when the pupil is dilated (such as at night). This drawback is also solved by the present invention, with the particular dimension of the intraocular implant as envisioned by the inventor.

As already known to those skilled in the art, Blavatskaya's principles show that the correction achieved through the implantation of such a device is directly related to its thickness and in inversely related to its diameter. So, the smaller the device and the greater the thickness, the larger the correction produced. Based on these principles the inventor has refined the design, dimensions, geometry and symmetry of the intracorneal implant to correct all the deficiencies of previous know devices.

While selected embodiments have been selected to be illustrated of the present invention, and specific examples have been described herein, it will be obvious to those skilled in the art that various changes and modifications may be aimed to cover in the appended claims. It will, therefore, be understood by those skilled in the art that the particular embodiments of the invention presented here are by way of illustration only, and are not meant to be in any way restrictive; therefore, numerous changes and modifications may be made, and the full use of equivalents resorted to, without departing from the spirit or scope of the invention as outlined in the appended claims.

The invention claimed is:

1. An intracorneal implant for the treatment of Keratoconus, comprising:
   first curved ring segment and a second curved ring segment sized and configured to be implanted facing each other in a circular configuration within a patient's intracorneal space, the first and second curved ring segments together forming a ring-like device,
   wherein the first and second curved ring segments are detached from each other when implanted,
   wherein the first and second curved ring segments are comprised of a transparent material,
   wherein each of the first and second curved ring segments has a too wall and a bottom wall of flat shape,
   wherein each of the first and second curved ring segments has an arcuate inner side wall and an arcuate outer side wall of rounded shape,
   wherein the ring-like device has an inner diameter represented by a distance between the inner side walls of the first and second curved ring segments, the inner diameter ranging between 5.0 mm to 5.25 mm,
   wherein the ring-like device has an outer diameter represented by a distance between the outer side walls of the first and second curved ring segments, the outer diameter ranging between 6.9 mm to 7.0 mm,
   wherein each of the first and second curved ring segments has an arc length of 160 degrees,
   wherein the first and second curved ring segments have a symmetrical cross section,
   wherein the first and second curved ring segments have a height from the too wall to the bottom wall ranging between 150 micrometers to 300 micrometers,
   wherein a maximum width for each of the top wall and the bottom wall in cross section is 0.75 mm,
   wherein a maximum width between the inner side wall and the outer side wall in cross section is 0.85 nm,
   wherein the first and second curved ring segments have rounded end portions.

2. The intracorneal implant of claim 1, wherein the ring-like device has an inner diameter of 5.20 mm.

3. The intracorneal implant of claim 1, wherein the ring-like device has an outer diameter of 7.0 mm.

4. The intracorneal implant of claim 1, wherein the first and second curved ring segments have a height ranging between 200 micrometers to 250 micrometers.

5. The intracorneal implant of claim 1, wherein the first and second curved ring segments are comprised of Poly (methyl methacrylate) (PMMA).

* * * * *

UNITED STATES PATENT AND TRADEMARK OFFICE
CERTIFICATE OF CORRECTION

PATENT NO. : 10,034,744 B1
APPLICATION NO. : 15/459902
DATED : July 31, 2018
INVENTOR(S) : Islam Mahmoud Hamdi Ibrahim Mostafa Page 1 of 1

It is certified that error appears in the above-identified patent and that said Letters Patent is hereby corrected as shown below:

In the Claims

At Column 7, Line 32, in Claim 1:
"has a too wall"
Should be:
"has a top wall and"

At Column 8, Line 15, in Claim 1:
"height from the too wall"
Should be:
"height from the top wall"

Signed and Sealed this
Twenty-ninth Day of January, 2019

Andrei Iancu
*Director of the United States Patent and Trademark Office*